(12) United States Patent
Yuan et al.

(10) Patent No.: US 11,655,423 B2
(45) Date of Patent: May 23, 2023

(54) PROCESS FOR SEPARATING ALKYLATION PRODUCT, ALKYLATION REACTION AND SEPARATION PROCESS, AND RELATED APPARATUS

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Qing Yuan, Beijing (CN); Junyi Mao, Beijing (CN); Zhenxing Zhu, Beijing (CN); Tao Huang, Beijing (CN); Zhihai Zhao, Beijing (CN); Yongxiang Li, Beijing (CN); Lifeng Hu, Beijing (CN); Xiaojin Tang, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 13 days.

(21) Appl. No.: 17/274,342

(22) PCT Filed: Sep. 6, 2019

(86) PCT No.: PCT/CN2019/104644
§ 371 (c)(1),
(2) Date: Mar. 8, 2021

(87) PCT Pub. No.: WO2020/048521
PCT Pub. Date: Mar. 12, 2020

(65) Prior Publication Data
US 2021/0324274 A1    Oct. 21, 2021

(30) Foreign Application Priority Data

Sep. 6, 2018    (CN) .................. CN201811039335

(51) Int. Cl.
*C10G 7/00*    (2006.01)
*B01D 3/06*    (2006.01)
(Continued)

(52) U.S. Cl.
CPC ............... *C10G 7/00* (2013.01); *B01D 3/007* (2013.01); *B01D 3/06* (2013.01); *B01D 3/143* (2013.01);
(Continued)

(58) Field of Classification Search
None
See application file for complete search history.

(56) References Cited

U.S. PATENT DOCUMENTS 3,097,250 A * 7/1963 Davies ..................... C07C 7/04
585/715
3,763,022 A 10/1973 Chapman
(Continued)

FOREIGN PATENT DOCUMENTS

| CN | 101550065 A | 10/2009 |
| CN | 202951270 U | 5/2013 |

(Continued)

*Primary Examiner* — Tam M Nguyen
(74) *Attorney, Agent, or Firm* — Novick, Kim & Lee, PLLC; Allen Xue

(57) ABSTRACT

A process for separating an alkylation product includes introducing a liquid phase alkylation product from an alkylation reaction unit into a first heat-exchanger directly or after being pressurized with a pressure pump and heat-exchanged with a vapor phase stream from the column top of a high-pressure fractionating column, then into a second heat-exchanger and subsequently into the high-pressure fractionating column. The vapor phase stream from the (Continued)

column top of the high-pressure fractionating column is heat-exchanged with the liquid phase alkylation product to be separated, a liquid phase stream from the column bottom of the high-pressure fractionating column is introduced into a low-pressure fractionating column and subjected to fractionation under a condition of 0.2 MPa-1.0 MPa, a low-carbon alkane is obtained from the column top of the low-pressure fractionating column, and a liquid phase stream obtained from the column bottom of the low-pressure fractionating column is an alkylation oil product.

13 Claims, 1 Drawing Sheet

(51) Int. Cl.

| | | |
|---|---|---|
| | *B01D 3/00* | (2006.01) |
| | *B01D 3/14* | (2006.01) |
| | *B01D 3/32* | (2006.01) |
| | *B01D 5/00* | (2006.01) |
| | *C07C 2/86* | (2006.01) |
| | *C07C 7/04* | (2006.01) |
| | *C10G 57/00* | (2006.01) |

(52) U.S. Cl.
CPC ............ *B01D 3/322* (2013.01); *B01D 5/0063* (2013.01); *B01D 5/0075* (2013.01); *C07C 2/865* (2013.01); *C07C 7/04* (2013.01); *C10G 57/005* (2013.01)

(56) References Cited

U.S. PATENT DOCUMENTS

| | | | |
|---|---|---|---|
| 4,182,924 A | * | 1/1980 | Chapman ................ C07C 7/005 585/723 |
| 5,986,158 A | | 11/1999 | Van Broekhoven et al. |
| 7,875,754 B2 | | 1/2011 | D'Amico |
| 2010/0197987 A1 | * | 8/2010 | Almering ................ C07C 7/005 585/671 |
| 2011/0232327 A1 | * | 9/2011 | Nanda .................... F25J 3/0219 62/620 |
| 2018/0079699 A1 | * | 3/2018 | Panditrao ................ C07C 2/66 |

FOREIGN PATENT DOCUMENTS

| | | |
|---|---|---|
| CN | 104109065 A | 10/2014 |
| CN | 105617706 A | 6/2016 |
| CN | 108211402 A | 6/2018 |
| CN | 108211403 A | 6/2018 |

* cited by examiner

PROCESS FOR SEPARATING ALKYLATION PRODUCT, ALKYLATION REACTION AND SEPARATION PROCESS, AND RELATED APPARATUS

The present application is a U.S. national phase entry of International Application No. PCT/CN2019/104644, filed on Sep. 6, 2019, which claims the priority to Chinese patent application 201811039335.9, filed on Sep. 6, 2018.

TECHNICAL FIELD

The present invention relates to a process for separating a mixture and a separation apparatus, in particular to a process for separating an alkylation product of low-carbon alkene and alkane and a separation apparatus.

BACKGROUND TECHNOLOGY

An alkylation oil is a clean high-octane gasoline blending component. Under the action of a strong acid, an isoalkane (mainly isobutane) and an alkene (C3-05 alkene) react to generate an alkylation oil mainly composed of isooctane. Alkylation technology can be divided into liquid acid alkylation and solid acid alkylation according to the catalyst form. The alkylation reaction of alkenes and alkanes is very complicated, the main reaction is the addition reaction of alkenes and alkanes, but various side reactions also occur at the same time, mainly including the superposition of alkenes, the cracking of macromolecules and the like. In order to increase the concentration of the reactant isobutane and to suppress the occurrence of side reactions such as the superposition of alkenes, it is necessary to maintain a high alkane/alkene ratio in the reaction system. In the sulfuric acid alkylation process currently used in industry, the external alkane/alkene ratio of the reactor feed is about 7-10, and the internal ratio is as high as several hundreds or even thousands; the hydrofluoric acid process also has a large isobutane recycle, with an external isobutane/alkene ratio of about 5-20, depending on the selected reactor configuration; for the solid acid alkylation technique, higher external and internal ratios are used, and the solid acid alkylation processes disclosed in U.S. Pat. Nos. 5,986,158 and 7,875,754 require using the external ratios of at least 5:1, preferably 16-32:1. The result of using a higher external ratio is a very low proportion of the alkylation oil in the stream from the reactor outlet: for the liquid acid process, the proportion of the alkylation oil to the inlet of the main fractionating column is about 10%-30%, and for the solid acid process, that proportion is even lower, typically less than 10%. The large isobutane recycle results in the high energy consumption in the main fractionating column, which is also the most significant cause for the higher energy consumption in the alkylation process. In the prior art, the energy consumption of the liquid acid process is about 100 kgEo/ton alkylation oil, and the energy consumption of the solid acid process is as high as 200 kgEo/ton alkylation oil. At least 80% of all energy consumption is used in the separation process of the alkylation oil and the recycled isobutane in the product, and the energy consumption is mainly caused by the fact that the condensation low-temperature heat of a large amount of low-carbon hydrocarbons cannot be effectively recovered and utilized.

SUMMARY OF THE INVENTION

The technical problem to be solved by the present invention is to provide a process and an apparatus for separating an alkylation product of low-carbon alkenes and alkanes, which can improve the heat utilization efficiency and remarkably reduce the energy consumption in the separation process of the alkylation product.

A process for separating an alkylation product, which is characterized in that a liquid phase alkylation product from an alkylation reaction unit is introduced into a first heat-exchanger directly or after being pressurized with a pressure pump and heat-exchanged with a vapor phase stream from the column top of a high-pressure fractionating column, then introduced into a second heat-exchanger and further heated to 100° C.-180° C., then introduced into the high-pressure fractionating column and subjected to fractionation under a condition of 2.0 MPa-6.0 MPa, the vapor phase stream from the column top of the high-pressure fractionating column is heat-exchanged with the liquid phase alkylation product to be separated, a liquid phase stream from the column bottom of the high-pressure fractionating column is introduced into a low-pressure fractionating column and subjected to fractionation under a condition of 0.2 MPa-1.0 MPa, a low-carbon alkane is obtained from the column top of the low-pressure fractionating column, and a liquid phase stream obtained from the column bottom of the low-pressure fractionating column is an alkylation oil product; wherein an inter-reboiler is provided to the low-pressure fractionating column, and the vapor phase stream from the column top of the high-pressure fractionating column is heat-exchanged in the first heat-exchanger and then used as the heating source for the inter-reboiler, preferably wherein the high pressure fractionating column is a flash column. An alkylation reaction and separation process comprises (1) an alkylation raw material is contacted with an acidic catalyst in an alkylation reaction unit to perform an alkylation reaction, and the material after the reaction is discharged as an alkylation product out of the alkylation reaction unit; (2) the liquid phase alkylation product from the alkylation reaction unit is introduced into a first heat-exchanger directly or after being pressurized with a pressure pump, and heat-exchanged with a vapor phase stream from the column top of a high-pressure fractionating column, then introduced into a second heat-exchanger and further heated to 100° C.-180° C., then introduced into the high-pressure fractionating column and subjected to fractionation under a condition of 2.0 MPa-6.0 MPa, the vapor phase stream from the column top of the high-pressure fractionating column is heat-exchanged with the liquid phase alkylation product to be separated, a liquid phase stream from the column bottom of the high-pressure fractionating column is introduced into a low-pressure fractionating column and subjected to fractionation under a condition of 0.2 MPa-1.0 MPa, a low-carbon alkane is obtained from the column top of the low-pressure fractionating column, and a liquid phase stream obtained from the column bottom of the low-pressure fractionating column is an alkylation oil product; an inter-reboiler is provided to the low-pressure fractionating column, and the vapor phase stream from the column top of the high-pressure fractionating column is heat-exchanged in the first heat-exchanger and then used as the heat source for the inter-reboiler.

An apparatus for separating an alkylation product comprises a first heat-exchanger, a second heat-exchanger, a high-pressure fractionating column and a low-pressure fractionating column, which are sequentially connected in series, wherein, the first heat-exchanger is provided with a stream to be separated (namely, the stream to be separated is directly introduced into the first heat-exchanger), an outlet of the second heat-exchanger is communicated with an inlet of the raw material for the high-pressure fractionating column, an inter-reboiler is provided to the low-pressure fractionating column, an outlet of the column bottom stream for the high-pressure fractionating column is communicated with an inlet of the raw material for the low-pressure fractionating column, an outlet of the column top stream for the high-pressure fractionating column is communicated with an inlet of the hotter fluid medium for the first heat-exchanger, an outlet of the hotter fluid medium for the first heat-exchanger, in one part, is communicated with an inlet of the column top reflux for the high-pressure fractionating column and in the other part, returns to an inlet of an alkylation reactor through the inter-reboiler of the low-pressure fractionating column.

The process and the apparatus for separating an alkylation product provided by the present invention have the following beneficial effects:

(1) Aiming at the characteristics of the large proportion and the low condensation potential temperature of the recycled stream in the alkylation product, the potential temperature of the recycled stream is increased by using a high-pressure flash evaporation method, and the heat is recovered by heat-exchanging with the alkylation product to be separated and providing an inter-reboiler to the low-pressure fractionating column, thereby the aims of saving energy and reducing consumption are fulfilled.

(2) A large part of the recycled stream is firstly separated through a high-pressure fractionating column, so that concentrating the alkylation oil in a low-pressure fractionating column is realized, the total amount of the vapor phase in the fractionating column is reduced, the improvement of the operation reasonability of the low-pressure fractionating column is facilitated, and the structure size of the unit equipment is greatly reduced.

(3) The equipments for the high-pressure fractionation and the low-pressure fractionation are simple, the operation difficulty is small, the control is easy, and the energy-saving effect is prominent.

(4) The technical solution of the present invention is particularly suitable for the separation of the alkylation reaction product obtained by using a solid acid catalyst.

Figure 1:
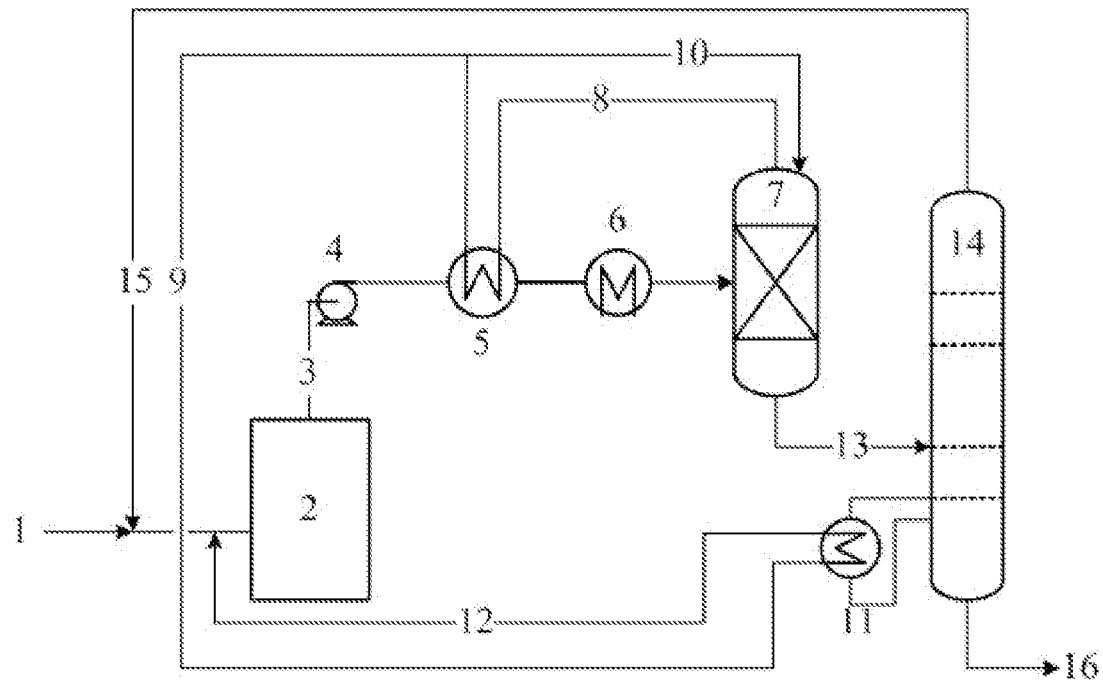
FIG. 1 is a schematic flow diagram for the process for separating an alkylation product provided by the present invention.

In said figures: 1—pipeline for the alkylation raw material, 2—alkylation reaction unit, 3—pipeline for the alkylation product, 4—liquid phase pressure pump, 5—first heat-exchanger, 6—second heat-exchanger, 7—high-pressure fractionating column, 11—inter-reboiler, 14—low-pressure fractionating column, 8, 9, 10, 12, 13, 15, 16, 17—pipelines.

DETAILED DESCRIPTION OF THE INVENTION

The specific embodiments of the present invention will be described in detail below with reference to the accompanying drawings. It should be understood that the specific embodiments described herein are only used to illustrate and explain the present invention and are not intended to limit the present invention.

1. Definition

Unless defined otherwise, all technical and scientific terms used herein have the same meanings as commonly understood by those skilled in the art to which this invention belongs. In case of conflict, the present specification, including definitions, will control. In the present invention, the pressure is expressed as gauge pressure; the operating pressure of the column is expressed as the column top pressure.

(1) Alkylation Reaction Unit

According to the present invention, the alkylation reaction refers to that an alkane (e.g. an alkane having 3-5 carbon atoms) is reacted with an alkene (e.g. an alkene having 3-5 carbon atoms) under pressure in the presence of a catalyst to form an alkane (particularly an isoalkane) having a longer chain, and the alkylation product is present in the state of liquid phase. In the alkylation reaction unit, a solid or liquid catalyst is used. In the case of a solid catalyst, the alkylation reaction product may exit the alkylation reactor and directly go to a subsequent separating unit. In the case of a liquid catalyst, the alkylation reaction unit further comprises an acid removal operation, and the acid-removed alkylation reaction product exits the alkylation reaction unit and goes to a subsequent separating unit. The alkylation reaction and the acid removal process and the associated apparatuses in the alkylation reaction unit are known in the art.

(2) Liquid Phase Alkylation Product

According to the present invention, the liquid phase alkylation product comprises unreacted C3-C5 alkanes (mass fraction: greater than 50%, for example 50-90%, 50-95%, or 50-99%), a small amount of the remaining alkenes (mass fraction: less than 10%, less than 9%, less than 8%, less than 7%, less than 6%, less than 5%, less than 4%, less than 3%, less than 2%, less than 1%), and a mixture having a distillation range of about 25° C.-about 220° C., especially about 25° C.-about 180° C. as the product (mass fraction: 1%-40%). In the case of the solid catalyst, the liquid phase alkylation product can contain 5%-15% of the mixture having a distillation range of about 25° C.-about 220° C., especially about 25° C.-about 180° C. as the product; and in the case of the liquid catalyst, the liquid phase alkylation product can contain 10%-30% of the mixture having a distillation range of about 25° C.-about 220° C., especially about 25° C.-about 180° C. as the product.

(3) Low-Carbon Alkane

In the present invention, the low-carbon alkane refers to C3-C5 hydrocarbons with isoalkanes (for example isobutane) as the main component, wherein the content of isoalkanes is higher than 50%, 60% or more, 70% or more, 80% or more, 90% or more, 95% or more, 96% or more, 97% or more, 98% or more, 99% or more, based on the total weight of the low-carbon alkane, and the low-carbon alkane also comprises other C3-C5 alkanes and alkenes.

(4) Alkylation Oil Product

In the present invention, the alkylation oil product refers to a mixture having a distillation range of about 25° C.-about 220° C., especially about 25° C.-about 180° C. The alkylation oil product is mainly composed of isoalkanes, which comprise greater than 80%, and has an alkene content of less than 2%, and an isooctane content of greater than 50%.

(5) Fractionating Column and Flash Column

In the present invention, the fractionating column comprises a feed inlet, a rectifying section, a stripping section, a column top condenser, a column bottom reboiler, an optional inter-condenser, and an optional inter-reboiler.

In the present invention, the flash column refers to such a fractionating column, which does not include the stripping section and the reboiler of a general fractionating column, and more particularly, which does not include the stripping section, the column bottom reboiler, the inter-condenser, and the inter-reboiler of a general fractionating column, but includes the feed inlet, the rectifying section, and the column top condenser of a general fractionating column.

(6) Alkylation Raw Material

In the present invention, the alkylation raw material refer to C3-C5 alkanes and C3-05 alkenes, wherein the molar ratio of alkane to alkene is 5-30:1, for example 5-15:1 or 8-20:1.

2. Process for Separating an Alkylation Product

In a basic embodiment of this section, the present invention provides a process for separating an alkylation product, which process comprises a liquid phase alkylation product from an alkylation reaction unit is introduced into a first heat-exchanger directly or after being pressurized with a pressure pump and heat-exchanged with a vapor phase stream from the column top of a high-pressure fractionating column, then introduced into a second heat-exchanger and further heated to 100° C.-180° C., then introduced into the high-pressure fractionating column and subjected to fractionation under a condition of 2.0 MPa-6.0 MPa, the vapor phase stream from the column top of the high-pressure fractionating column is heat-exchanged with the liquid phase alkylation product to be separated, a liquid phase stream from the column bottom of the high-pressure fractionating column is introduced into a low-pressure fractionating column and subjected to fractionation under a condition of 0.2 MPa-1.0 MPa, a low-carbon alkane is obtained from the column top of the low-pressure fractionating column, and a liquid phase stream obtained from the column bottom of the low-pressure fractionating column is an alkylation oil product; wherein an inter-reboiler is provided to the low-pressure fractionating column, and the vapor phase stream from the column top of the high-pressure fractionating column is heat-exchanged in the first heat-exchanger and then used as the heating source for the inter-reboiler.

In one embodiment in combination with one or more of the embodiments mentioned in this section, the high pressure fractionating column is preferably a flash column. In the flash column, there is provided with a filler having a certain height or column plate(s), a reflux configuration is provided at the column top, and no reboiler is provided at the column bottom.

In one embodiment in combination with one or more of the embodiments mentioned in this section, the low-pressure fractionating column is a conventional packed column or a conventional plate column, a reflux configuration is provided at the column top, and a reboiler is provided at the column bottom.

In one embodiment in combination with one or more of the embodiments mentioned in this section, the temperature difference between the liquid phase alkylation product and the vapor phase stream that are heat-exchanged in the first heat-exchanger is at least 10° C., more preferably at least 30° C.

In one embodiment in combination with one or more of the embodiments mentioned in this section, the liquid phase alkylation product has a temperature of 0° C.-100° C. and a pressure of 0.1 MPa-4.0 MPa; the high pressure fractionating column has an operating temperature of 100° C.-180° C. and a column top reflux ratio of 0.1-2.0; the low-pressure fractionating column has a column top temperature of 20° C.-80° C., for example 30° C.-60° C., a column bottom temperature of 100° C.-180° C., and a column top reflux ratio of 0.5-5.0. In one embodiment in combination with one or more of the embodiments mentioned in this section, the inter-reboiler is provided in the middle of the low-pressure fractionating column, and the stream introduced from the inter-reboiler has a temperature of 20° C.-120° C., for example 30° C.-120° C. The middle of the low-pressure fractionating column refers to a position between 30% and 70% by height of the low-pressure fractionating column from the top to the bottom. The low-pressure fractionating column may be a plate column or a packed column. In the case of the plate column, the middle of the low-pressure fractionating column refers to a position between 30% and 70% by height of all column plates from the top to the bottom. In the case of the packed column, the middle of the low-pressure fractionating column refers to a position between 30% and 70% by height of the filler from the top to the bottom.

In one embodiment in combination with one or more of the embodiments mentioned in this section, the liquid phase alkylation product pressurized by a pressure pump has a pressure of 2.0 MPa-6.0 MPa.

In one embodiment in combination with one or more of the embodiments mentioned in this section, after being heated by the heat-exchanging with the first heat-exchanger and the second heat-exchanger, the liquid phase alkylation product has a temperature of 100° C.-180° C. and a vapor phase fraction of 0.3-1.0. The vapor phase fraction refers to the percentage content of the vapor phase in the stream.

In one embodiment in combination with one or more of the embodiments mentioned in this section, the pressure pump is a liquid phase pump, preferably a pipe-type pump, more preferably a centrifugal pump.

In one embodiment in combination with one or more of the embodiments mentioned in this section, the vapor phase stream from the high-pressure fractionating column, which is heat-exchanged in the first heat-exchanger, is wholly condensed into the liquid phase, the condensed liquid phase, in one part, returns to the column top of the high-pressure fractionating column as reflux, and in the other part, returns to the alkylation reaction unit, the low carbon alkane from the column top of the low-pressure fractionating column returns to the alkylation reaction unit.

In one embodiment in combination with one or more of the embodiments mentioned in this section, the alkylation product to be separated and the vapor phase stream from the column top of the high-pressure flash column are heat-exchanged in the first heat-exchanger, preferably in the manner of the cross-flow heat-exchanging, and the heat-exchanged alkylation product to be separated has a temperature of 70-150° C., for example 90-140° C.

In one embodiment in combination with one or more of the embodiments mentioned in this section, all heat-exchangers are in the manner of the cross-flow heat-exchanging.

In one embodiment in combination with one or more of the embodiments mentioned in this section, the operating pressure of the high-pressure fractionating column is higher than the operating pressure of the low-pressure fractionating column by 2-4 MPa, for example, 2-2.5 MPa, for example greater than 2 MPa and less than 2.5 MPa.

In one embodiment in combination with one or more of the embodiments mentioned in this section, the high pressure fractionating column has a column top vapor phase temperature of 100° C.-180° C., a column bottom liquid phase temperature of 100° C.-180° C. and higher than the column top vapor phase temperature, a column top reflux ratio of 0.1-2.0 (for example 0.5-0.6), and an operating pressure of 0.1 MPa-4.0 MPa (for example 2.0 MPa-4.0 MPa, still further 2.9 MPa-3.5 MPa), and the low-pressure fractionating column has a column top temperature of 20° C.-80° C. (for example 30° C.-60° C.), a column bottom temperature of 100° C.-180° C., a column top reflux ratio of 0.5-5.0 (for example 1), and an operating pressure of 0.2 MPa-1.0 MPa (for example 0.3 MPa-0.6 MPa).

3. Alkylation Reaction and Separation Process

In a basic embodiment of this section, the present invention provides an alkylation reaction and separation process, comprising (1) an alkylation raw material is contacted with an acidic catalyst in an alkylation reaction unit to perform an alkylation reaction, and the material after the reaction is discharged as an alkylation product out of the alkylation reaction unit; (2) the liquid phase alkylation product from the alkylation reaction unit is introduced into a first heat-exchanger directly or after being pressurized with an optional pressure pump, and heat-exchanged with a vapor phase stream from the column top of a high-pressure fractionating column, then introduced into a second heat-exchanger and further heated to 100° C.-180° C., then introduced into the high-pressure fractionating column and subjected to fractionation under a condition of 2.0 MPa-6.0 MPa, the vapor phase stream from the column top of the high-pressure fractionating column is heat-exchanged with the liquid phase alkylation product to be separated, a liquid phase stream from the column bottom of the high-pressure fractionating column is introduced into a low-pressure fractionating column and subjected to fractionation under a condition of 0.2 MPa-1.0 MPa, a low-carbon alkane is obtained from the column top of the low-pressure fractionating column, and a liquid phase stream obtained from the column bottom of the low-pressure fractionating column is an alkylation oil product; an inter-reboiler is provided to the low-pressure fractionating column, and the vapor phase stream is heat-exchanged in the first heat-exchanger and then used as the heat source for the inter-reboiler.

In one embodiment in combination with one or more of the embodiments mentioned in this section, the high pressure fractionating column is a flash column with reflux at the column top and no reboiler at the column bottom.

In one embodiment in combination with one or more of the embodiments mentioned in this section, the alkylation catalyst can be a liquid acid catalyst or a solid acid catalyst.

In one embodiment in combination with one or more of the embodiments mentioned in this section, a liquid acid catalyst is used in the alkylation reaction unit, and the liquid acid catalyst is selected from sulfuric acid, hydrofluoric acid or an ionic liquid. The alkylation reaction condition in which sulfuric acid is used as the catalyst is as follows: the reaction temperature is 0° C.-50° C., the absolute reaction pressure is 0.1 MPa-1.0 MPa, and the external alkane/alkene ratio is 5-15:1.

In one embodiment in combination with one or more of the embodiments mentioned in this section, a solid acid catalyst is used in the alkylation reaction unit, and the solid acid catalyst is one or more of a heteropoly acid catalyst, a heteropoly acid salt catalyst, a molecular sieve catalyst, a super acid catalyst, an ion exchange resin and an acid-treated oxide catalyst. The alkylation reaction condition in which a solid acid is used as the catalyst is preferably as follows: the reaction temperature is 50° C.-100° C., the absolute reaction pressure is 1.0 MPa-4.0 MPa, and the external alkane/alkene ratio is 8-20:1. The alkylation product to be separated from the alkylation reaction unit has a temperature of 0° C.-100° C.

In one embodiment in combination with one or more of the embodiments mentioned in this section, a loaded molecular sieve catalyst, for example a platinum-loaded Y-type molecular sieve is used in the alkylation reaction unit. Preferably, the loaded molecular sieve catalyst is prepared as follows: a NaY type molecular sieve with an FAU structure is subjected to the sodium-removal modification on the molecular sieve through a step of ammonium-exchanging, and then subjected to the loading of platinum on the catalyst by an ion-exchanging method, wherein the metal content is 0.3 wt %; finally, the obtained platinum-loaded molecular sieve and alumina are uniformly mixed in a ratio of 70:30, and the mixture is further dried and calcined to prepare a strip-shaped catalyst.

In one embodiment in combination with one or more of the embodiments mentioned in this section, the mass fraction of the alkylation oil product in the alkylation product is 1%-40% (for example 5%-15% or 10%-30%), and the remaining components are unreacted low-carbon alkanes and others.

In one embodiment in combination with one or more of the embodiments mentioned in this section, the liquid phase alkylation product to be separated is pressurized through a liquid phase pump, then successively heat-exchanged through the first heat-exchanger and further heated through the second heat-exchanger, and then introduced into the high-pressure flash column. The heated stream that is introduced into the high-pressure flash column has a vapor phase fraction of 0.3-1.0. The vapor phase fraction refers to the percentage of the vapor phase relative to the whole stream.

In one embodiment in combination with one or more of the embodiments mentioned in this section, the high pressure fractionating column has an operating pressure of 2.0 MPa-6.0 MPa and an operating temperature of 100° C.-180° C., and a condensation reflux configuration is provided at the column top with a reflux ratio of 0.1-2.0. The vapor phase stream from the column top of the high-pressure flash column is heat-exchanged with the liquid phase alkylation product to be separated and is wholly condensed into the liquid phase, so that the recovery and utilization of latent heat is realized. The liquefied vapor phase stream, in one part, returns to the column top of the high-pressure flash column as reflux, and in the other part, directly mixed and heat-exchanged with the stream to the reactor inlet, thereby greatly increasing the heat utilization and the heat-exchanging efficiency.

In one embodiment in combination with one or more of the embodiments mentioned in this section, the column bottom stream for the high pressure fractionating column is introduced into the low-pressure fractionating column for the separation of the alkylation oil and the remaining low-carbon alkanes, and the operating condition of the low-pressure fractionating column preferably comprises: the pressure is 0.2 MPa-1.0 MPa, the column top reflux ratio is 0.5-5.0, and the column bottom temperature is 100-180° C.

In one embodiment in combination with one or more of the embodiments mentioned in this section, the streams from the column top of the high-pressure fractionating column and the column top of the low-pressure fractionating column return to the reactor inlet, and are mixed with the fresh feed, heated-exchanged, and then introduced into the reactor for the alkylation reaction.

4. Apparatus for Separating an Alkylation Product

In a basic embodiment of this section, the present invention provides an apparatus for separating an alkylation product, comprising a first heat-exchanger, a second heat-exchanger, a high-pressure fractionating column and a low-pressure fractionating column, which are sequentially connected in series, wherein, the first heat-exchanger is provided with a stream to be separated (namely, the stream to be separated is directly introduced into the first heat-exchanger), an outlet of the second heat-exchanger is communicated with an inlet of the raw material for the high-pressure fractionating column, an inter-reboiler is provided to the low-pressure fractionating column, an outlet of the column bottom stream for the high-pressure fractionating column is communicated with an inlet of the raw material for the low-pressure fractionating column, an outlet of the column top stream for the high-pressure fractionating column is communicated with an inlet of the hotter fluid medium for the first heat-exchanger, an outlet of the hotter fluid medium for the first heat-exchanger, in one part, is communicated with an inlet of the column top reflux for the high-pressure fractionating column and in the other part, returns to an inlet of a reactor through the inter-reboiler of the low-pressure fractionating column.

One or more of the embodiments mentioned in the above Section 2 may be used in any of the embodiments mentioned in Section 4 to form a new technical solution. For example, it is preferable that the high-pressure fractionating column is a flash column with a condensation tank and a reflux pipe at the column top and no reboiler at the column bottom. In one embodiment in combination with one or more of the embodiments mentioned in this section, the apparatus for separating an alkylation product also comprises a pressure pump, wherein the pressure pump is disposed between the stream to be separated and the first heat-exchanger, an inlet of the pressure pump is provided with the stream to be separated, an outlet of the pressure pump is communicated with the first heat-exchanger, and the pressure pump is a liquid phase pump. More preferably, it is a centrifugal pump.

5. Alkylation Reaction and Separation Apparatus

In a basic embodiment of this section, the present invention provides an alkylation reaction and separation apparatus, comprising an alkylation reaction unit and the apparatus for separating an alkylation product mentioned in the above Section 4, wherein an outlet of the alkylation reaction unit is communicated with the first heat-exchanger or an inlet of the pressure pump of the apparatus for separating an alkylation product, and the alkylation reaction unit is a liquid acid alkylation reaction unit or a solid acid alkylation reaction unit. Preferably, the alkylation reaction unit is a solid acid alkylation reaction unit.

6. Schematic Technical Solution

The process of the present invention is described in detail below with reference to the accompanying drawings. FIG. 1 is a schematic flow diagram of the alkylation reaction and separation process provided by the present invention. As shown in FIG. 1, a fresh alkylation raw material 1 is mixed with recycled streams 9/12 and 15 in a certain proportion, and the resulting mixture is heat-exchanged to the temperature required by the reaction and then introduced into an alkylation reactor 2 to perform the reaction. A stream 3 from the reactor outlet is subjected to the pressure adjustment with a liquid phase pressure pump 4, heat-exchanged with a stream 8 from the column top of the high-pressure flash column 7 through an interior heat-exchanger 5, then heated to a certain temperature through an external heater 6, introduced into the high-pressure flash column 7, and subjected to the separation of vapour and liquid phases in the flash column 7. The vapor phase stream 8 from the column top is heat-exchanged with the stream 3 from the reactor outlet through the interior heat-exchanger 5 and wholly condensed into liquid phase. In one part, the condensed liquid phase 9 returns to the reactor inlet and is directly mixed with the raw material 1 and the recycled stream 15, the resulting mixture is heat-exchanged and introduced into the reactor 2 for the further reaction; and in the other part, the liquid phase 10 returns to the top of the high-pressure flash column 7 as reflux in order to control the content of the alkylation oil in the stream 9 recovered from the column top. A stream 13 from the column bottom of the high-pressure flash column is introduced into the a low-pressure fractionating column 14 for the separation of the alkylation oil and the low-carbon alkane, wherein the low-carbon alkane 15 recovered from the column top is recycled, and the alkylation oil 16 from the column bottom exits the apparatus.

7. Examples

The present invention will be further described below in conjunction with specific examples, but the present invention is not limited thereby.

Comparative Example 1

Figure 2:
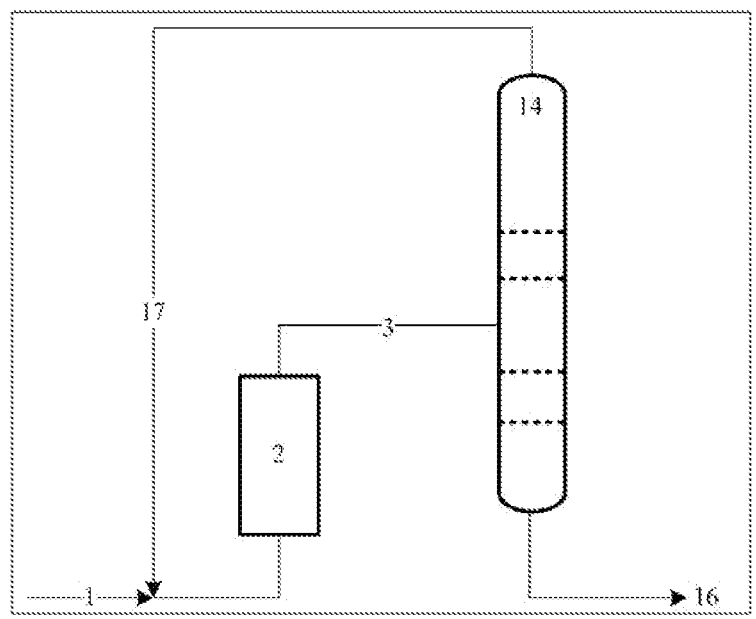
FIG. 2 is a schematic flow diagram for the process for separating an alkylation product used in Comparative Examples 1 and 2.

The schematic flow diagram of Comparative Example 1 is shown in FIG. 2.

In the alkylation reaction unit, C4 alkanes and alkenes were subjected to the alkylation reaction in the presence of a liquid acid catalyst. A concentrated sulfuric acid with a concentration of 96 wt % (commerically available) was used as the catalyst. An isoalkane in the alkylation raw material was mainly composed of isobutane and commercially available from Beijing Huayuan Gas Chemical Industry Co., Ltd, and its composition was listed in Table 1; and a C4 residue after ether removal, obtained from an MTBE apparatus of Refinery Division, Sinopec Yanshan Petrochemical Co., Ltd., was used as the alkene raw material, and its composition was listed in Table 1. The alkylation reaction temperature was 5° C., the reaction pressure was 0.6 MPa, and the external alkane/alkene ratio was 8:1.

The alkylation product from the outlet of the alkylation reactor had a temperature of 5° C. and a pressure of 0.6 MPa, and was subjected to the acid removal and then directly introduced into the low-pressure fractionating column for the separation of the alkylation oil and the C4 stream. The content of the alkylation oil in the stream to be separated was 20%, and the rest was the unreacted isobutane and n-butane. The low-pressure fractionating column was run at an operating pressure of 0.3 MPa, a column top temperature of 32° C., a column bottom temperature of 123° C., and a reflux ratio of 1.0.

The properties of the feed and the product of the low-pressure fractionating column were shown in Table 2, and the main fractionation energy consumption comparison was shown in Table 3.

Example 1

Example 1 illustrates the effect of the process for separating an alkylation product provided by the present invention.

The reaction and separation flow shown in FIG. 1 was used, the alkylation reaction unit was identical to that in Comparative Example 1, and the stream to be separated, i.e. the alkylation product obtained from the alkylation reactor was identical to that in Comparative Example 1.

The system and process for separating the alkylation product described in the present invention was used, and the specific operating conditions were as follows: the outlet pressure of the pressure pump was 3.6 MPa, the outlet temperature of the heat-exchanger for the cold stream was 76° C., the outlet temperature of the external heater was 160° C., the vapor phase fraction was 0.6, the high-pressure flash column was run at an operating pressure of 3.5 MPa, a column top vapor phase temperature of 148° C., a reflux ratio of 0.6, and a column bottom liquid phase temperature of 157° C. The vapor phase from the column top was cooled to 80° C. after being heat-exchanged with the stream from the reactor outlet and condensed into the whole liquid phase, and then cooled to 50° C. after being heat-exchanged with the inter-reboiler of the low-pressure fractionating column. The stream from the column bottom of the high-pressure flash column was introduced into the low-pressure fractionating column for the separation of the alkylation oil and the C4 stream, an inter-reboiler of the low-pressure fractionating column was provided to the rectifying section, the leaving temperature of the stream was 36° C. and the returning temperature was 37° C., and other operation conditions were identical to those of Comparative Example 1. The properties of the feed and the product of the low-pressure fractionating column were shown in Table 2, and the main fractionation energy consumption comparison was shown in Table 3.

Comparative Example 2

The schematic flow diagram of Comparative Example 2 is shown in FIG. 2.

In the alkylation reaction unit, C4 alkanes and alkenes were subjected to the alkylation reaction in the presence of a solid acid catalyst. The alkylation raw material was identical to that of Comparative Example 1, the used catalyst was a loaded molecular sieve catalyst obtained as follows: a NaY type molecular sieve (produced by Sinopec Catalyst Division) with an FAU structure was subjected to the sodium-removal modification on the molecular sieve through the steps of ammonium-exchanging and the like, and then subjected to the loading of platinum on the catalyst by an ion-exchanging method, wherein the metal content was 0.3 wt %; finally, the obtained platinum-loaded molecular sieve and alumina were uniformly mixed in a ratio of 70:30, and the mixture was further dried and calcined to prepare a strip-shaped catalyst. The alkylation reaction was carried out at a temperature of 60° C., a pressure of 3.1 MPa and an external alkane/alkene ratio of 25:1. The content of the alkylation oil in the stream from the outlet of the alkylation reactor was 5.6% with the remainder being the unreacted isobutane and n-butane.

The stream from the outlet of the alkylation reactor was directly introduced into the low-pressure fractionating column for the separation of the alkylation oil and the C4 stream, and the low-pressure fractionating column was run at a column top pressure of 0.6 MPa, a column top temperature of 53° C., a column bottom temperature of 159° C., and a reflux ratio of 1.0.

The properties of the feed and the product of the low-pressure fractionating column were shown in Table 2, and the main fractionation energy consumption comparison was shown in Table 3.

Example 2

Example 2 illustrates the effect of the process for separating an alkylation product provided by the present invention.

The reaction and separation flow shown in FIG. 1 was used, the alkylation reaction unit was identical to that in Comparative Example 2, and the outlet pressure of the reactor was 3.0 MPa, and the pressure of the high-pressure flash column was 2.9 MPa, therefore no pressure pump was neccesarily disposed between them. The outlet temperature of the first heat-exchanger for the cold stream was 115° C., the outlet temperature of the second heat-exchanger was 135° C., the vapor phase fraction was 0.9, the high-pressure flash column was run at a column top vapor phase temperature of 128° C., a reflux ratio of 0.5, and a column bottom liquid phase temperature of 133° C. The vapor phase from the column top of the flash column was cooled to 120° C. after being heat-exchanged with the stream from the reactor outlet and condensed into the whole liquid phase, and then cooled to 80° C. after being heat-exchanged with the inter-reboiler of the low-pressure fractionating column. The stream from the column bottom of the high-pressure flash column was introduced into the low-pressure fractionating column for the separation of the alkylation oil and the C4 stream, an inter-reboiler of the low-pressure fractionating column was provided to the rectifying section, the leaving temperature of the stream was 65° C. and the returning temperature was 90° C., and other operation conditions were identical to those of Comparative Example 2.

The properties of the feed and the product of the low-pressure fractionating column were shown in Table 2, and the main fractionation energy consumption comparison was shown in Table 3.

TABLE 1

Properties of the reaction raw materials

| Component | | Mass Fraction (%) |
|---|---|---|
| Isoalkane | Propane | 1.7 |
| | Isobutane | 95.2 |
| | n-butane | 2.0 |
| | Butene | 1.1 |
| C4 residue after ether removal | n-butene and iso-butene | 0.94 |
| | n-butane | 4.96 |
| | Cis-2-butene | 24.57 |
| | Trans-2-butene | 12.33 |
| | Isobutane | 57.20 |

TABLE 2

Properties of the feed and the product of the low-pressure fractionating column

| Item | Comparative Example 1 | Example 1 | Comparative Example 2 | Example 2 |
|---|---|---|---|---|
| Content of Feedstock Oil, % | 20.0 | | 5.6 | |
| Content of the oil introduced into the low-pressure fractionating column, % | 20.0 | 27.1 | 5.6 | 12.4 |

TABLE 2-continued

Properties of the feed and the product of the low-pressure fractionating column

| Item | Comparative Example 1 | Example 1 | Comparative Example 2 | Example 2 |
|---|---|---|---|---|
| D86 of Alkylation Oil | | | | |
| IBP | 26.8 | 26.3 | 24.8 | 24.5 |
| 10 | 57.0 | 57.8 | 58.2 | 58.7 |
| 30 | 99.1 | 99.8 | 99.8 | 99.6 |
| 50 | 104.8 | 104.6 | 105.2 | 105.3 |
| 70 | 113.7 | 113.4 | 113.9 | 113.1 |
| 90 | 126.5 | 126.7 | 126.8 | 126.3 |
| FBP | 180.5 | 180.9 | 180.7 | 181.7 |

TABLE 3

Separation Energy Consumption Comparison

| Heat Consumption MJ/t Alkylation Oil | External Heater | Reboiler of Fractionating Column | Total | Reduced Steam Consumption % |
|---|---|---|---|---|
| Comparative Example 1 | 0 | 3136 | 3136 | — |
| Example 1 | 1464 | 322 | 1786 | 43.1 |
| Comparative Example 2 | 0 | 10196 | 10196 | — |
| Example 2 | 3490 | 281 | 3771 | 63.0 |

The invention claimed is:

1. A process for separating an alkylation product, comprising:
introducing a liquid phase alkylation product from an alkylation reaction unit into a first heat-exchanger as a cold stream to exchange heat with a vapor phase stream from a column top of a high-pressure fractionating column, wherein the liquid phase alkylation product is pressurized using a pressure pump or not pressurized;
introducing the liquid phase alkylation product exiting from the first heat-exchanger into a second heat-exchanger as a cold stream;
heating the liquid phase alkylation product in the second heat-exchanger and further heated to 100° C.;
introducing the liquid phase alkylation product exiting from the second heat-exchanger into the high-pressure fractionating column for fractionation under a condition of 2.0 MPa-6.0 MPa;
introducing the vapor phase stream from the column top of the high-pressure fractionating column into the first heat-exchanger as a hot stream;
introducing a liquid phase stream from a column bottom of the high-pressure fractionating column into a low-pressure fractionating column for fractionation under a condition of 0.2 MPa-1.0 MPa,
obtaining a low-carbon alkane from the column top of the low-pressure fractionating column, and a liquid phase stream from the column bottom of the low-pressure fractionating column as an alkylation oil product, and
heating a material stream from the low-pressure fractionating column as a cold stream in an inter-reboiler using at least a part of the vapor phase stream from the column top of the high-pressure fractionating column exiting from first heat-exchanger as a hot stream; and
feeding the heated material stream from the inter-reboiler to the low-pressure fractionating column.

2. The process for separating an alkylation product according to claim 1, wherein the high-pressure fractionating column is a flash column.

3. The process for separating an alkylation product according to claim 1, wherein a temperature of the material stream introduced into the inter-reboiler is 20° C.-120° C.

4. The process for separating an alkylation product according to claim 1, wherein a temperature difference between the cold and hot streams in the first heat-exchanger or the inter-reboiler is at least 10° C.

5. The process for separating an alkylation product according to claim 1, wherein the liquid phase alkylation product has a temperature of 0° C.-100° C. and a pressure of 0.1 MPa-4.0 MPa; the high-pressure fractionating column has an operating temperature of 100° C.-180° C. and a column top reflux ratio of 0.1-2.0; the low-pressure fractionating column has a column top temperature of 20° C.-80° C., a column bottom temperature of 100° C.-180° C., and a column top reflux ratio of 0.5-5.0.

6. The process for separating an alkylation product according to claim 1, wherein that the liquid phase alkylation product pressurized by the pump has a pressure of 2.0 MPa-6.0 MPa.

7. The process for separating an alkylation product according to claim 1, wherein, after being heated in the first heat-exchanger and the second heat-exchanger, the liquid phase alkylation product has a temperature of 100° C.-180° C. and a vapor phase fraction of 0.3-1.0.

8. The process for separating an alkylation product according to claim 1, wherein the pressure pump is a liquid phase centrifugal pump.

9. The process for separating an alkylation product according to claim 1, wherein the vapor phase stream from the high-pressure fractionating column is condensed in the first heat-exchanger into a liquid stream, wherein a first portion of the liquid stream is returned to the column top of the high-pressure fractionating column as reflux, and a second portion of the liquid stream is introduced into the inter-reboiler, the liquid stream exiting the inter-reboiler is introduced to the alkylation reaction unit, and the low carbon alkane from the column top of the low-pressure fractionating is introduced to the alkylation reaction unit.

10. An alkylation reaction and separation process, comprising: contacting an alkylation raw material with an acidic catalyst in an alkylation reaction unit to perform an alkylation reaction; and
discharging a liquid phase alkylation product from an alkylation reaction unit,
separating the liquid phase alkylation product according to the process of claim 1.

11. The alkylation reaction and separation process according to claim 10, wherein the high-pressure fractionating column is a flash column.

12. The alkylation reaction and separation process according to claim 10, wherein the alkylation catalyst is a solid acid catalyst selected from a heteropoly acid catalyst, a heteropoly acid salt catalyst, a molecular sieve catalyst, a super acid catalyst, an ion exchange resin, an acid-treated oxide catalyst, and mixtures thereof.

13. The alkylation reaction and separation process according to claim 10, wherein the alkylation reaction condition comprises: the reaction temperature is 50° C.-100° C., the absolute reaction pressure is 1.0 MPa-4.0 MPa, and the external alkane/alkene ratio is 8-30:1.

* * * * *